United States Patent [19]

Homolko et al.

[11] Patent Number: 4,801,428
[45] Date of Patent: Jan. 31, 1989

[54] BLOOD SAMPLE SEDIMENTATION TEST KIT

[75] Inventors: Johannes Homolko, La Croix Des Ayes; Pierre T. Dader, Grenoble; Bernard Assier, Seyssins, all of France

[73] Assignee: Becton, Dickinson and Company, Franklin Lakes, N.J.

[21] Appl. No.: 923,365

[22] Filed: Oct. 27, 1986

[51] Int. Cl.[4] .................. G01N 21/01; G01N 31/22
[52] U.S. Cl. ........................................ 422/61; 422/58; 422/65; 422/73; 422/102; 436/47; 73/61.4; 33/143 B
[58] Field of Search ............ 422/65, 73, 58, 102, 422/61; 436/47; 73/61.4; 33/143 B

[56] References Cited

U.S. PATENT DOCUMENTS

| | | | |
|---|---|---|---|
| 3,812,707 | 5/1974 | Proni et al. | 73/61.4 |
| 4,168,955 | 9/1979 | Allington | 436/47 |
| 4,388,407 | 6/1983 | Lepain et al. | 436/177 |
| 4,592,227 | 6/1986 | Poncept | 436/70 |

FOREIGN PATENT DOCUMENTS 2604127.4 5/1986 Fed. Rep. of Germany .

*Primary Examiner*—Barry S. Richman
*Assistant Examiner*—Lynn Kummert
*Attorney, Agent, or Firm*—Robert P. Grindle

[57] ABSTRACT

A test kit is provided for measuring the erythrocyte sedimentation rate automatically in the original blood collection tube which is of a size and is so modified to be used for the resulting testing that no further blood transfer is required. The blood collection tube is evacuated to the desired level to obtain the desired quantity of blood to be collected and contains the proper quantity of anticoagulant. The test kit of the invention includes one or more tube-like slots for maintaining the blood collection tubes stable and in a vertical orientation for the testing procedure. Each slot includes a tube sleeve vertically adjustable in each slot. Each sleeve includes an appropriate Westergren scale which is moved with the sleeve to accommodate the positioning of the initial top level of the red blood cells in the sample.

7 Claims, 2 Drawing Sheets

BLOOD SAMPLE SEDIMENTATION TEST KIT

BACKGROUND AND STATEMENT OF THE INVENTION

This invention relates to an erythrocyte sedimentation rate (ESR) test which is used as a simple, non-specific blood screening test for inflammatory diseases. The original test was laid out in 1921 by A. Westergren and the basic procedure, in the sense of reading the sedimentation rate of the blood sample, has remained virtually unchanged to date. This ESR test is routinely used in general practitioners' offices, hospital wards and labs to screen for increased inflammatory activity in blood as sort of a basic initial test. Very high ESR values in otherwise non-symptomatic patients may be an indication of such diseases as rheumatic diseases, cirrhosis of the liver, malignant tumors, and anemia. Moreover, the ESR test is routinely used to monitor corticosteroid therapy for rheumatic diseases. Because of this, the ESR test is frequently the first test performed on patients prior to the initiation of other tests.

Originally the Westergren method utilized a blood sample transfer technique in which a syringe was used to obtain a blood sample, and then the blood sample was transferred into reusable glass pipettes. This blood transfer involved the potential hazard to clinicians being exposed to an open blood sample.

Such open blood tests were modified in the past with a device which is described in German Petty Patent No. 26-04-127.4 dated May 15, 1986, which is incorporated herein by reference in its entirety. In that patent, a device is described in which the sedimentation testing process occurs directly in the reagent tube into which the blood sample is initially introduced. For this reason, the reagent tube already contains the anticoagulant substance to be mixed with the blood sample introduced, and is evacuated to facilitate the taking of a blood sample. The device includes an upright frame with a plurality of slots for the introduction of the reagent tubes into the slots. Scales are printed on the face of the frame behind the area where the reagent tubes are positioned in the slots. The clinician, once a sample has been introduced into the reagent tube, and the stopper replaced on the tube, inverts the tube or shakes the tube in order to co-mingle the sample with the anticoagulant already in the tube.

Then, the reagent tube is introduced into the slot provided in the device described. The tube is manually moved in a vertical direction in the slot. The slots or bores are arranged to have a diameter to provide a snug fit for the reagent tubes introduced into them. In this way, the tubes are held frictionally at the vertical level which the clinician positions the tube. By doing so, the clinician may move the tube vertically up and down in order to position the initial upper level of the red blood cells in the sample to be at the zero mark on the scale printed on the frame behind the tube. Then, after an appropriate period of time, usually at one hour and two hour intervals after the introduction of the initial sample, measurements are taken to measure the sedimentation rate of the red blood cell level in the samples introduced into the device.

While such an arrangement is a vast improvement over the original arrangement wherein blood samples had to be transferred from one container to another, thus exposing the clinician to the raw blood sample, such a device still has certain limitations. For example, the printed scale on the upright facing of the device is located behind the reagent tubes when they are positioned for a reading. Since the tubes themselves generally have a diameter of ten millimeters, a very pronounced paralax effect may take place in attempting to read the scale through the tube itself, depending upon what angle the user of the stand tries when reading the values on the scale. Differences of several millimeters are possible which may cause an incorrect reading, as will be understood by practitioners-in-the-art.

Also, moving the reagent tubes up and down within the bore in which they are held in the stand has a tendency to be awkward for certain people and there may be differences in the readings caused simply by variations in production tolerances of tube diameter versus the bores in which the tubes are moved up and down. Also, this variation may be such that the tubes are not held properly at the position required, and any slippage, of course, will modify the final reading obtained. A further minor difficulty has to do with the labeling required for identifying the individual samples in the reagent tubes. Any identification pasted on the tube has the effect of interfering with any readings being taken of the scale positioned behind the tube.

With this invention, by contrast, a new assembly is provided in which the reagent tubes are placed in one or more individual vertically positioned slots. Each of the slots includes a movable sleeve upon which the printed scale for reading the sedimentation rate of the blood sample in the tube is provided. The sleeves are vertically movable, rather than the reagent tubes which the sleeves surround, by a positive drive arrangement in the form of an individual knob for each tube. The individual knobs include a rubber sleeve on the central axial portion or axis of the knob assembly which rubber sleeve engages frictionally with the vertically movable sleeves in the slots to cause them to move upwardly or downwardly depending upon the rotation of the knob involved. A positive drive is provided in such a way that the sleeves move precisely as the knob is turned and are maintained in the appropriate vertical position at which they are set by the user. Thus, the user does not need to move or handle the reagent tube once it is introduced into the slots of the assembly of the invention here. The tube remains positioned as it is and only the vertical sleeve which has an open bottom and which surrounds the tube is moved in order to adjust the scale to the proper level of the sample introduced into the reagent tube initially.

Because of this, there is no variation in the movement of the reagent tube itself, since it never moves once it is introduced into the stand of the invention until the readings are completed. Moreover, because of the precise frictional drive between the adjusting knob and the surrounding vertically movable sleeve, there is no variation in movement once the initial setting has been made. Finally, because the scale is outside the actual reagent tube, there is no variation in the reading of the scale because of any distortion of the view of the reader through the reagent tube as with the prior art. It should be pointed out, finally, that because the reagent tubes are not disturbed or moved in any way during the sedimentation cycle, there is no vibration which would have the effect of distorting the final values obtained from the test procedure.

As purely illustrative of a device of the invention, one may not the attached drawings in which an assembly is shown with ten vertical slots for simultaneously reading ten different blood samples taken from as many as ten different patients, as desired. As will be understood by practitioners-in-the-art, each of the reagent tubes introducers into the assembly shown will have, prior to the introduction of the blood sample, an anti-coagulant material. Generally, this material will be a 0.11 Molar trisodium citrate solution. This will be introduced into each individual reagent tube in a quantity which will provide four parts of freshly collected blood from a patient to one part of the trisodium citrate solution. As will be understood by practitioners-in-the-art, each reagent tube is shaken or inverted so as to mix the anticoagulant material with the freshly collected blood sample prior to introduction into the assembly of the invention for carrying out the sedimentation test.

Figure 1:
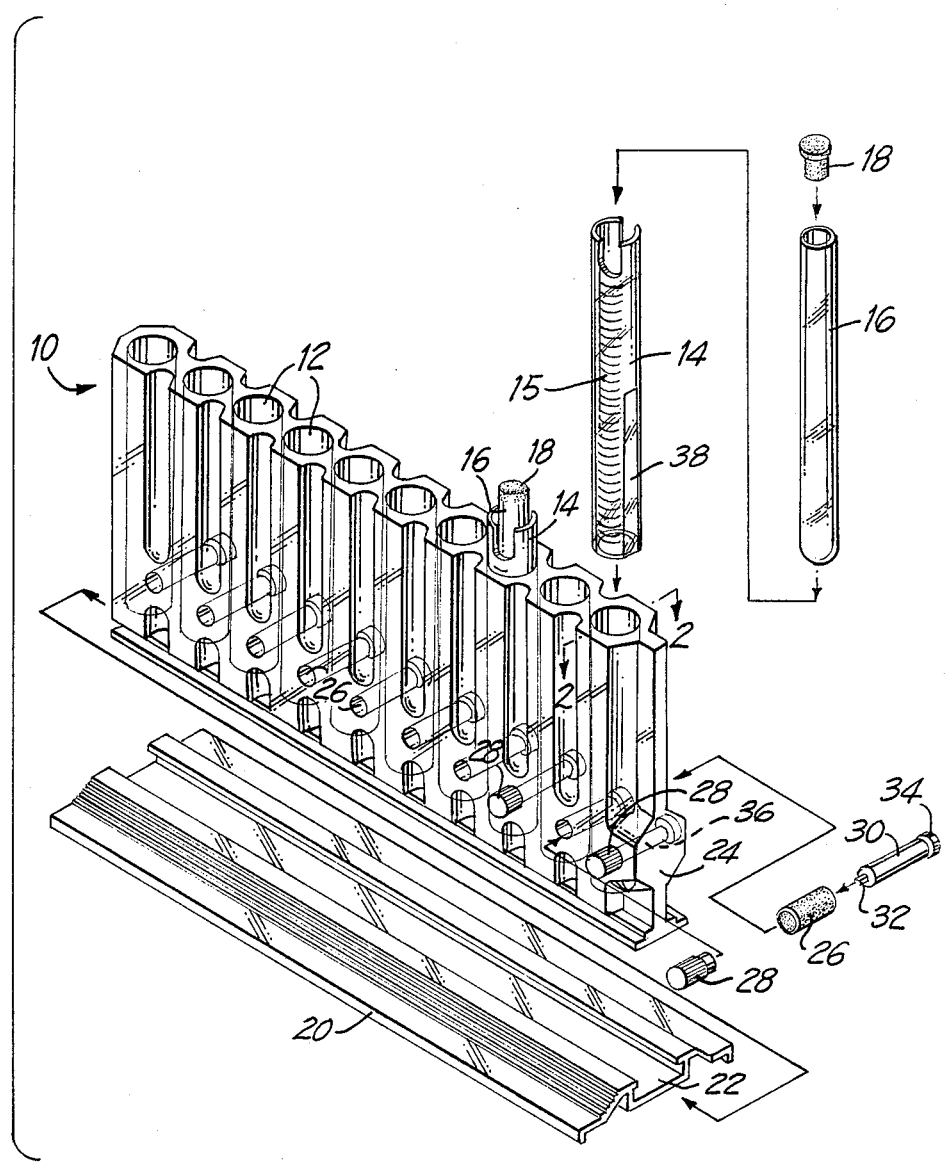
FIG. 1 is an exploded perspective view of the rack assembly of the invention showing an assembly having ten vertical slots for receiving ten separate individual samples. It will be understood by practitioners-in-the-art, however, that a larger or smaller number of slots may be used in an individual assembly depending upon the quantity required or desired for a particular facility.

Referring to the drawings, in which like reference characters refer to like parts throughout the several views thereof, a sedimentation rack assembly according to the invention is shown indicated generally at 10. As can be seen, assembly 10 is an elongated vertical rack assembly having ten separate vertical slots 12 interposed therein. Preferably, the assembly will be comprised of a plastic material which may be molded into the form shown. The assembly 10 will be comprised of a clear material so as to allow the user to look through the assembly to view the individual samples being tested in the assembly, as will be described in more detail below.

As can be seen in FIG. 1, assembly 10 has ten vertical slots 12 for receiving in each slot 12 a separate sleeve tube 14. Each sleeve tube 14 is vertically movable in its individual slot 12. Each tube 14, on one side thereof adjacent the bottom has a flat indentation 38 which is used as a portion of the frictional drive assembly for moving each sleeve tube 14 vertically up and down in its respective slot 12.

As can be seen in FIG. 1, the rack assembly 10 is supported in a base 20. In this connection, the molding process of rack assembly 10 is such as to provide an integral foot structure 24 which cooperates with the slot 22 in base 20 for sliding engagement. Thus, the integral foot arrangement is slid into and through slot 22 to support rack assembly 10 in its desired vertical orientation on base 20.

As can be seen in FIG. 1, each individual reagent tube 16 with its respective stopper 18, once a blood sample is introduced therein, is inserted into its respective slot 12 in the rack assembly 10. In this connection, prior to such introduction, it will be understood that each slot 12 already has introduced therein a vertically movable sleeve tube 14. Once this procedure takes place, the user then determines the top level of the red blood cells in the individual sample introduced in each of the slots 12. When this happens, the user then turns knob 28 in order to rotate the rubber sleeve 36 on the axis of knob 28.

The rubber sleeve 36 engages the flat surface 38 in a frictional drive which causes the raising or lowering of the individual sleeve tube 14 in slot 12, so that the zero line of the scale 15 on sleeve tube 14 coincides with the red blood cell top level of the freshly introduced blood sample in the individual reagent tube 16 of interest. Thereafter, each individual reagent tube 16 remains in the slot, with the adjustment made as described above, for a specified period of time. As mentioned above, this is usually one hour and two hour intervals to take a measurement of the sedimentation rate of the red blood cells in the blood sample to determine the presence or absence of a disease in the blood sample taken.

Figure 2:
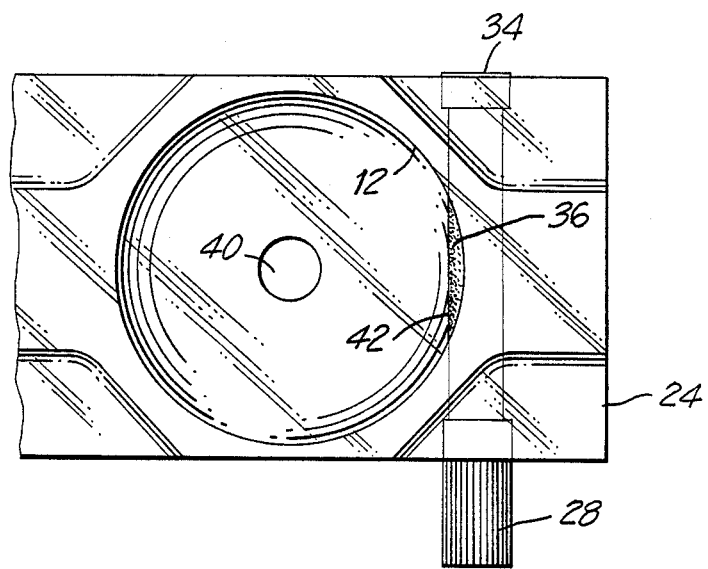
FIG. 2 is a view taken along lines 2—2 of FIG. 1.

With respect to the knob assembly used for the frictional drive, in accordance herewith, as can be seen in FIGS. 1 and 2, knob 28 includes a cooperating axial drive arrangement 30 with an integral portion 32 which is inserted into knob 28 for holding the various parts together. Frictional sleeve 36, as will be understood, is engaged over the axial drive portion 30 of knob 28. The opposite end of the knob assembly includes an abutment portion 34 which holds the knob assembly in is respective bore 26, extending through the rack assembly 10. As can be seen in FIG. 2, the frictional sleeve 36, which may be rubber for example, has a surface 42 which extends into the vertical bore of the individual slots 12 for cooperating with the flat surface portion 38 of the individual sleeve tubes 14 inserted into the slots 12. Thus, a precise vertical movement of sleeve tubes 14 take place simply by turning the knob 28 in either direction, as required. Each slot 12, as shown in FIG. 2, includes a bottom bore or opening 40 to facilitate cleaning.

Thus, as will be understood by practitioners-in-the-art, a new simplified rack assembly is provided for testing simultaneously one or more blood samples to determine the sedimentation rate of the red blood cell content thereof. The assembly includes a simplified arrangement for adjusting the scale used to set the level of the red blood cell content of each sample upon introduction of the reagent tube into the rack assembly. There is no requirement of blood transfer once the sample is introduced into the reagent tube, and the reagent tube, once introduced into the rack assembly of the invention is not moved or disturbed in any way to disturb the sedimentation rate for the final correct reading of the sedimentation rate. As can be seen, further, the arrangement is a simplified arrangement allowing for one or two vertical slots for testing one or two reagent samples simultaneously, or many more tubes may be introduced into the same assembly by a simple production arrangement for molding clear plastic materials into the form shown. It will be understood, however, that such a rack assembly may be comprised of glass, as required or depending upon the limitations of materials in a particular vicinity. Because of the simplified arrangement, in accordance herewith, it will be understood that the device of the invention may be manufactured by mass production techniques in large quantities without any expensive processing procedures. Accordingly, the arrangement herein is highly advantageous commercially.

While the apparatus herein disclosed forms a preferred embodiment of this invention, this invention is not limited to this specific apparatus, and changes can be made therein without departing from the scope of the invention which is defined in the appended claims. For example, while the sleeve for creating the frictional drive of the invention here on the knob assembly is described as being rubber, it will be understood that a variety of different materials may be utilized for bringing about the frictional drive required. Moreover, as discussed above, plastics or glass may be utilized, provided the material of the rack assembly itself is a clear material for the proper viewing and reading of the various blood samples being scrutinized.

What is claimed is:

1. An assembly for testing the erythrocyte sedimentation rate of at least one blood sample wherein the sample is not moved during testing, comprising
   (a) a vertically positioned transparent rack assembly body;
   (b) a plurality of vertically positioned slots in said body for receiving a blood reagent tube therein;
   (c) a transparent sleeve positioned for vertical movement in each of said plurality of slots;
   (d) an adjusting means adjacent each of said plurality of slots, each said adjusting means extending horizontally through said body and into a respective slot associated therewith, for frictional engagement with a respective vertically movable sleeve positioned within said respective slot;
   (e) cooperating means on each said adjusting means for frictionally engaging said respective adjacent vertically movable sleeve for moving said vertically movable sleeve from one position to another in said respective slot; and
   (f) scale means on each of said vertically movable sleeves for measuring a level of blood sample contained in a blood reagent tube introduced into a respective vertically positioned slot containing said vertically movable sleeve.

2. The assembly of claim 1, wherein each adjusting means adjacent a respective slot includes
   (a) a knob extending outwardly from said assembly body;
   (b) an axial drive bar connected to said knob and extending through said assembly body; and
   (c) a frictional drive sleeve extending over said drive bar for frictional engagement with a respective vertically movable sleeve.

3. The assembly of claim 2, wherein each cooperating means includes
   (a) a flat vertical drive surface on a respective vertically movable sleeve;
   (b) said drive surface extending vertically from a bottom edge of said respective vertically movable sleeve to a point spaced from the bottom edge thereof; and said respective frictional drive sleeve extending into a respective vertically positioned slot for frictionally engaging said flat vertical drive surface on said respective vertically movable sleeve.

4. The assembly of claim 1, further comprising
   (a) an elongated base for supporting said rack assembly body; and
   (b) cooperating attaching means on said body and said base for sliding attaching engagement of said elongated base and said rack assembly body.

5. The assembly of claim 1, further comprising
   (a) at least one reagent tube for obtaining a blood sample, said at least one tube for insertion into one of said plurality of vertically positioned slots in said assembly body;
   (b) each said at least one reagent tube having an open end and a closed end;
   (c) a stopper for closing the open end of said at least one reagent tube; and
   (d) an anticoagulant material in said at least one reagent tube, said anticoagulant material for mixing with a blood sample introduced into said at least one tube.

6. The assembly of claim 5, wherein
   (a) said anticoagulant material is a citrate solution.

7. The assembly of claim 1, wherein
   (a) said assembly body is comprised of a member selected from the group consisting of transparent plastic and glass.

* * * * *